United States Patent
Liu et al.

(10) Patent No.: US 8,344,042 B2
(45) Date of Patent: Jan. 1, 2013

(54) BIODEGRADABLE SYNTHETIC BONE COMPOSITES

(75) Inventors: Gao Liu, Oakland, CA (US); Dacheng Zhao, Shenzhen (CN); Eduardo Saiz, London (GB); Antoni P. Tomsia, Pinole, CA (US)

(73) Assignee: The Regents of the University of California, Oakland, CA (US)

( * ) Notice: Subject to any disclaimer, the term of this patent is extended or adjusted under 35 U.S.C. 154(b) by 359 days.

(21) Appl. No.: 12/633,708

(22) Filed: Dec. 8, 2009

(65) Prior Publication Data

US 2010/0179243 A1 Jul. 15, 2010

Related U.S. Application Data

(63) Continuation of application No. PCT/US2008/066346, filed on Jun. 9, 2008.

(60) Provisional application No. 60/942,988, filed on Jun. 8, 2007.

(51) Int. Cl.
*A61L 24/06* (2006.01)
*C08K 3/32* (2006.01)
*C08F 261/06* (2006.01)
*A61F 2/28* (2006.01)
*C08G 63/08* (2006.01)

(52) U.S. Cl. ........ 523/115; 523/113; 523/409; 424/422; 424/423; 424/426; 424/487; 524/417; 525/312; 623/23.61; 528/354

(58) Field of Classification Search .................. 523/115, 523/113, 409; 424/422, 423, 426, 487; 524/417; 525/312; 623/23.61; 528/354
See application file for complete search history.

(56) References Cited

U.S. PATENT DOCUMENTS

| 3,297,033 | A | 1/1967 | Schmitt et al. |
| 5,461,034 | A | 10/1995 | Rodan et al. |
| 6,479,460 | B1 | 11/2002 | Bab et al. |
| 8,022,040 | B2 | 9/2011 | Bertozzi et al. |
| 2004/0161444 | A1 | 8/2004 | Song et al. |
| 2005/0196702 | A1* | 9/2005 | Bryant et al. ................. 430/311 |
| 2007/0098799 | A1 | 5/2007 | Zhang et al. |
| 2007/0254011 | A1* | 11/2007 | Schnabelrauch et al. ..... 424/426 |
| 2008/0275171 | A1 | 11/2008 | Song et al. |
| 2008/0279908 | A1 | 11/2008 | Bertozzi et al. |

FOREIGN PATENT DOCUMENTS

| WO | 2004/056321 A2 | 7/2004 |
| WO | 2006/062776 A2 | 6/2006 |
| WO | 2006/091653 A2 | 8/2006 |
| WO | 2007/035296 A2 | 3/2007 |

OTHER PUBLICATIONS

An, Y. H. et al. (2000). "Pre-Clinical in Vivo Evaluation of Orthopaedic Bioabsorbable Devices," Biomaterials 21:2635-2652.

(Continued)

*Primary Examiner* — Michael Pepitone
(74) *Attorney, Agent, or Firm* — Robin C. Chiang; Lawrence Berkeley; National Laboratory

(57) ABSTRACT

The invention provides for a biodegradable synthetic bone composition comprising a biodegradable hydrogel polymer scaffold comprising a plurality of hydrolytically unstable linkages, and an inorganic component; such as a biodegradable poly(hydroxyethylmethacrylate)/hydroxyapatite (pHEMA/HA) hydrogel composite possessing mineral content approximately that of human bone.

22 Claims, 5 Drawing Sheets

OTHER PUBLICATIONS

Bourque, H. et al. (2001). "Investigation fo the Poly(L-Lactide)/Poly(D-Lactide) Stereocomplex at the Air-Water Interface by Polarization Modulation Infrared Reflection Absorption Spectroscopy," Langmuir 17:5842-5849.

Foppiano, S. et al. (2007). "Bioactive Glass Coatings Affect the Behavior of Osteoblast-Like Cells," Acta Biomaterialia 3:765-771.

Gilding, D. K. et al. (Dec. 1979). "Biodegradable Polymers for Use in Surgery-Polyglycolic/Poly(Actic Acid) Homo- and Copolymers:1," Polymer 20:1459-1464.

Gomez-Vega, J. M. et al. (2000). "Bioactive Glass Coatings with Hydroxypatite and Bioglass Particles on Ti-Based Implants. 1. Processing," Biomaterials 21:105-111.

Hollinger, J. O. et al. (1995). "Bone Repair and a Unique Class of Biodegradable Polymers: The Poly(alpha-Esters)," Chapter 9 in Biomedical Applications of Synthetic Biodegradable Polymers, Hollinger, J. O., ed., CRC Press, Boca Raton, FL, 197-222.

International Search Report and Written Opinion mailed Sep. 18, 2008, for PCT Application No. PCT/US08/66346 filed Jun. 9, 2008, 7 pages.

Khelfallah, N.S. et al. (2006). "Synthesis of a New PHEMA/PEO Enzymatically Biodegradable Hydrogel," Macromolecular Rapid Communications 27:1004-1008.

Kohn, J. et al. (2004). "Bioresorbable and Bioerodible Materials," Chapter 2.7 In Biomaterials Science: An Introduction to Materials in Medicine, 2nd Edition, Ratner, B. D. et al., eds, Elsevier Academic Press, San Diego, CA, 115-127.

Kulkarni, R. K. et al. (1966). "Polylactic Acid for Surgical Implants," Archives of Surgery 93:839-343.

Kulkarni, R. K. et al. (1971). "Biodegradable Poly(Lactic Acid) Polymers," Journal of Biomedical Material Research, 5:169-181.

MacroPore, Inc. (2001). "Macropore Resorbable Technology: An Overview", Scientific Data Series in Resorbable Fixation, available at http://www.mastbio.com/pdf/resorb_overview.pdf, (8 pages).

Middleton, J. C. et al. (Mar. 1, 1998). "Synthetic Biodegradable Polymers as Medical Devices," MMDI Medical Device and Diagnostic Industry New Products and Suppliers, available at http://www.mddionline.com/article/synthetic-biodegradable-polymers-medical-devices, (9 pages).

Qiao, M. et al. (2005). "Injectable Biodegradable Temperature-Responsive PLGA-PEG-PLGA Copolymers: Synthesis and Effect of Copolymer Composition on the Drug Release from the Copoylmer-Based Hydrogels," International Journal of Pharmaceutics 294:103-112.

Ratner, B. D. (1996). "The Engineering of Biomaterials Exhibiting Recognition and Specificity," Journal of Molecular Recognition 9:617-625.

Rokkanen, P. U. (2002). "Bioabsorbable Polymers for Medical Applications with an Emphasis on Orthopedic Surgery," Chapter 20 in Polymeric Biomaterials, Dumitriu, S., ed., Marchel Dekker, Inc., New York, NY, 545-562.

Sawhney, A. S. et al. (1993). "Bioerodible Hydrogels Based on Photopolymerized Poly(Ethylene Glycol)-Co-Poly-(alpha-Hydroxy Acid) Diacrylate Macromers," Macromolecules 26(4):581-587.

Service, R. F. (2000). "Tissue Engineers Build New Bone," Science 289:1498-1500, available at http://www.sciencemag.org/content/289/5484/1498.full, (4 pages).

* cited by examiner

US 8,344,042 B2

BIODEGRADABLE SYNTHETIC BONE COMPOSITES

CROSS-REFERENCE TO RELATED APPLICATIONS

This application claims priority as a continuation application to International Patent Application No. PCT/US2008/066346, filed Jun. 9, 2008, which claims priority to U.S. Provisional Application Ser. No. 60/942,988, filed Jun. 8, 2007, all of which are hereby incorporated by reference.

STATEMENT OF GOVERNMENTAL SUPPORT

The invention described and claimed herein was made in part utilizing funds supplied by the U.S. Department of Energy under Contract No. DE-AC02-05CH11231 and the National Institutes of Health under Grant No. 5R01 DE015633. The government has certain rights in this invention.

FIELD OF THE INVENTION

This invention relates generally to biodegradable synthetic bone composite materials.

BACKGROUND OF THE INVENTION

As the world population ages there is an increasing demand for biomaterials to assist or replace organ functions and improve quality of life (R. F. Service, *Science*, 2000, 289, 1498). Traditional biomaterials for bone replacement are developed from materials designed originally for engineering applications that have serious shortcomings associated to the fact that their physical properties do not match those of the surrounding tissue and, unlike natural bone, cannot self-repair or adapt to changing physiological conditions. Thus, an ideal solution, and a scientific research challenge, is to develop bone-like biomaterials (or tissue engineering scaffolds) that will be treated by the host as normal tissue matrices and will integrate with bone tissue while they are actively resorbed or remodeled in a programmed way, with controlled osteogenic activity. This material will requires an interconnected pore network with tailored surface chemistry for cell growth and penetration, and the transport of nutrients and metabolic waste. It should degrade at a controlled rate matching the tissue repair rates producing only metabolically acceptable substances and releasing drugs and/or stimulating the growth of new bone tissue at the fracture site by slowly releasing bone growth factors (e.g., bone morphogenic protein or transforming growth factor-$\beta$) throughout its degradation process. In addition, its mechanical properties should match those of the host tissues and the strength and stability of the material-tissue interface should be maintained while the material is resorbed or remodeled.

SUMMARY OF THE INVENTION

The present invention provides for a biodegradable bone-like composition comprising a biodegradable hydrogel polymer scaffold comprising a plurality of hydrolytically unstable linkages, and an inorganic component.

The biodegradable hydrogel polymer scaffold comprises the following structure: a plurality of linear chains, wherein each linear chain comprises a crosslinker which links the linear chain to another linear chain, and each crosslinker comprises a hydrolytically unstable linkage.

The present invention further provides for a bone or dental implant comprising the composition described. The present invention further provides for a composition described which has undergone biodegradation, and optionally has a mammalian cells grown into the biodegraded composition. In a particular embodiment, the mammalian cells are human cells. In particular, the cells are bone cells, such as osteoblasts.

The present invention further provides for a method for synthesizing the biodegradable bone-like composition comprising: (a) providing the reagents for synthesizing the composition described comprising the polymer described above and an inorganic component; (b) polymerizing the reagents to form the composition under a condition suitable for the polymerization reaction.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a peptide" includes a plurality of such peptides, and so forth.

These and other objects, advantages, and features of the invention will become apparent to those persons skilled in the art upon reading the details of the invention as more fully described below.

Biodegradable Hydrogel Polymer Scaffold

Figure 2:
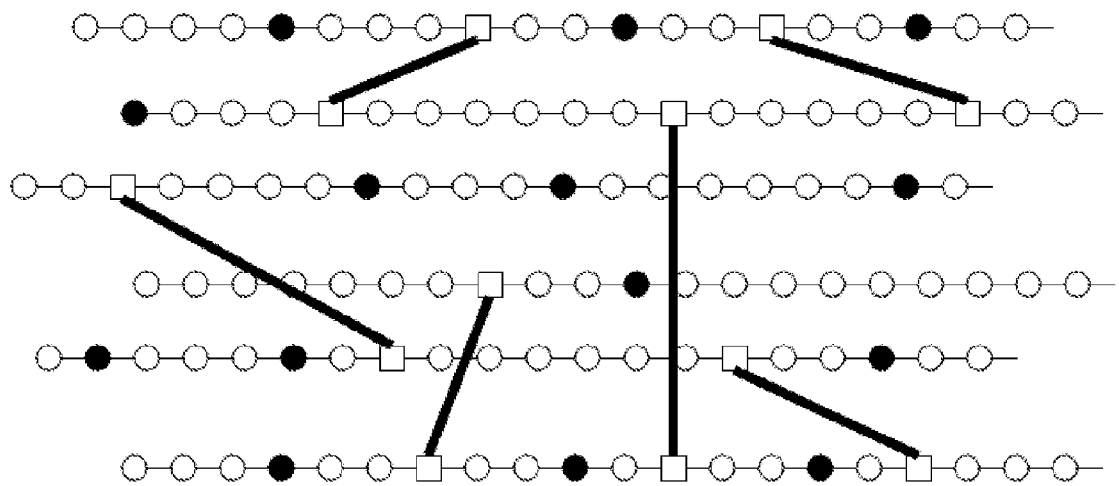
FIG. 2 shows a schematic of an example of a polymer of the present invention. The open circle represents a first repeating subunit (such as a HEMA monomer), the filled circle represents a second repeating subunit (such as a MA monomer), and the two squares connected by a bold line represents the crosslinker.

An illustration of an exemplary of the biodegradable flexible hydrogel polymer is shown in FIG. 2. In particular, the composition comprises three-dimensional composites comprising a biodegradable flexible hydrogel polymer, wherein the composites have a high inorganic content and strong mechanical properties yet exhibit elastic properties. The polymer can designed with a variety of ratios of different subunits or monomers to produce a polymer with a desired biodegradation rate. Using the method of measuring the biodegradation rate taught in the Example, one skilled in the art can determine the biodegradation of a particular polymer designed. Further, the composites can be used for various applications calling for a strong yet flexible hybrid material comprised of organic and inorganic components. The organic-to-inorganic ratio can be made wide ranging, allowing the tailoring of the flexibility and stiffness of the composite to suit various needs.

Each linear chain of the biodegradable hydrogel polymer scaffold comprises one or more repeating subunits of different structures with the following structure:

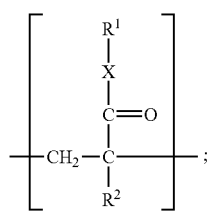

Formula I wherein $R^1$ is H or a lower alkyl, $R^2$ is H or a lower alkyl, and X is O, S or NH.

In some embodiments, the number of repeating subunits in each chain is between 10 and 500,000. In some embodiments, the number of repeating subunits in each chain is between 100 and 100,000.

The term "lower alkyl" means any substituted or unsubstituted, saturated or unsaturated, branched or unbranched, or cyclic hydrocarbon, or a combination thereof, with 1 to 20 carbon atoms, including substituted alkyl residues. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. In particular embodiments, the lower alkyl means a substituted or unsubstituted methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl.

In particular embodiments, the plurality of linear chains comprises two or more repeating subunits of different structures, wherein each linear chain comprises two or more repeating subunits of different structures. In some embodiments, each linear chain comprises two repeating subunits of different structures. Each linear chain comprises one or more crosslinker by which the linear chain is linked to another linear chain.

In some embodiments, X is O. In some embodiments, $R^1$ is H, —$CH_2OH$, —$CH_2CH_2OH$, —$CH_2CH_2CH_2OH$, —$CH(CH_3)CH_2OH$, —$CH_2CH(CH_3)OH$, —$C(CH_3)_2OH$, or —$C_4H_8$—OH. In certain embodiments, $R^1$ is H, —$CH_2OH$, —$CH_2CH_2OH$, —$CH_2CH_2CH_2OH$, —$CH(CH_3)CH_2OH$, —$CH_2CH(CH_3)OH$, —$C(CH_3)_2OH$, or —$C_4H_8$—OH. In some embodiments, $R^2$ is H.

In certain embodiments, each linear chain comprises a first repeating subunit wherein X is O, $R^2$ is H, and $R^1$ is H; and a second repeating subunit wherein X is O, $R^2$ is H, and $R^1$ is —$CH_2CH_2OH$.

In some embodiments, each crosslinker comprises a compound of the following structure:

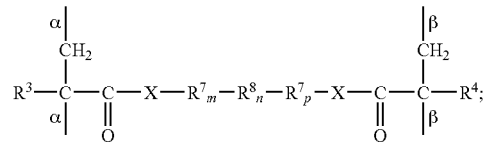

Formula III wherein $R^3$ is H or a lower alkyl; $R^4$ is H or a lower alkyl; X is O, S or NH; $R^7$ is —$R^9COO$—, —$R^9C(OR^{10})(OR^{11})O$—, —$R^9CONH$—, or —$R^9CON(R^{10})$—; $R^8$ is —$C_qH_{2q}$—O—, wherein q is an integer from 0 to 3; m, n, and p are each independently an integer from 1 to 500,000;

$R^9$ is —$C_rH_{2r}$—, wherein r is an integer from 0 to 3;

$R^{10}$ and $R^{11}$ are each independently —$C_sH_{2s}$—$CH_3$, wherein s is an integer from 0 to 3; and the α bonds connect two repeating subunits of a first linear chain, and the β bonds connect two repeating subunits of a second linear chain.

In some embodiments, X is O. In some embodiments, $R^3$ is H, —$CH_2OH$, —$CH_2CH_2OH$, —$CH_2CH_2CH_2OH$, —CH $(CH_3)CH_2OH$, —$CH_2CH(CH_3)OH$, —$C(CH_3)_2OH$, or —$C_4H_8$—OH. In certain embodiments, $R^4$ is H, —$CH_2OH$, —$CH_2CH_2OH$, —$CH_2CH_2CH_2OH$, —$CH(CH_3)CH_2OH$, —$CH_2CH(CH_3)OH$, —$C(CH_3)_2OH$, or —$C_4H_8$—OH. In some embodiments, $R^3$ and $R^4$ are the same. In some embodiments, $R^3$ and $R^4$ are H. In some embodiments, $R^7$ is —$CH_2COO$—, —$CH(CH_3)COO$—, or —$CH(CH_2CH_3)COO$—. In some embodiments, $R^8$ is —$CH_2CH_2O$—, —$CH_2CH_2CH_2O$—, —$CH(CH_3)CH_2O$—, —$CH_2CH(CH_3)O$—, —$C(CH_3)_2O$—, or —$C_4H_8$—O—.

In certain embodiments, X is O, $R^3$ and $R^4$ are H, $R^7$ is —$CH(CH_3)COO$—, and $R^8$ is —$CH_2CH_2O$—.

In some embodiments, m, n, and p are each independently an integer from 1 to 100,000. In certain embodiments, the sum of m, n and p is an integer from 1 to 100,000 or 1 to 500,000.

Each crosslinker comprises a biodegradable ester, anhydride, orthoester, amide, or peptide bond. In some embodiments, each crosslinker comprises an ethylene oxide or polyethylene oxide (PEO) with a polylactic acid or polyglycolide dimethacrylate or dimethacrylamide. Polylactide or polyglycolide can be polymerized at both ends of PEG to form a hybrid polymer. Dimethacrylate or dimethacrylamide can then capped at both ends of the hybrid polymer. The capped hybrid polymer can then be polymerized with suitable monomers and inorganic molecules to form the biodegradable bone-like composition.

Exemplary hybrid polymers include:

Formula II

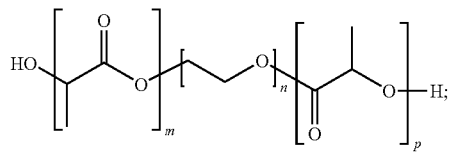

wherein m, n and p are as described above.

The composition comprising a biodegradable hydrogel polymer scaffold comprising a plurality of hydrolytically unstable linkages, and an inorganic component is synthesized, for example using the method described in Example 1.

Exemplary molecules that can be used in the polymerization reaction to produce the crosslinker in the polymer scaffold include:

Formula IV

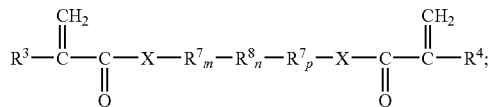

wherein X, $R^3$, $R^4$, $R^7$ and $R^8$, and m, n, and p, are as described herein.

Exemplary molecules that can be used in the polymerization reaction to produce the one or more repeating subunits in the linear chains include:

Formula V

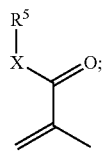

wherein $R^5$ is H or a lower alkyl, and X is —O—, —S— or —NH—.

In some embodiments, X is O. In some embodiments, $R^5$ is H, —$CH_2OH$, —$CH_2CH_2OH$, —$CH_2CH_2CH_2OH$, —$CH(CH_3)CH_2OH$, —$CH_2CH(CH_3)OH$, —$C(CH_3)_2OH$, or —$C_4H_8$—OH. In certain embodiments, $R^5$ is H, —$CH_2OH$, —$CH_2CH_2OH$, —$CH_2CH_2CH_2OH$, —$CH(CH_3)CH_2OH$, —$CH_2CH(CH_3)OH$, —$C(CH_3)_2OH$, or —$C_4H_8$—OH. Such exemplary molecules include 2-hydroxyethyl methacrylate (HEMA) and methyacrylate (MA).

Polylactic acid (PLA) can be synthesized into two different stereoisomeric forms, polylevolactic acid [poly(l-lactide)] (LPLA) and polydextrolactic acid [poly(d-lactide)] (DPLA), where the l and d are optical isomers. A racemic mixture is poly(dl-lactide) (PDL). All of these forms of PLA are suitable for use for this invention. LPLA and DPLA and copolymers are synthesized through ring opening polymerization of lactide. The ring opening of the mixture of the two will result in an unpredictable order of methyl group diads and tetrads. Polyglycolide (PG) is a commercial available biodegradable linear aliphatic polyester. Copolymers of polylactide and polyglycolide can be synthesized to arrive at a polymer with a different range of properties than the homopolymer. A copolymer that contains between 25-75% of one polymer will be amorphous and therefore will degrade in a faster time than either of the polymers would alone. Copolymers are an attractive choice for different uses, because the properties (mechanical, degradation times) can be tailored to fit the application. Homopolymers and copolymers consisting of gylcolide and lactide have been approved by the U.S. FDA for use in the body.

The composition and polymer scaffold can be further modified in any way taught in U.S. patent application Ser. Nos. 60/434,596; 60/655,986; 60/631,660; and 10/740,739 (U.S. Pat. Application Pub. No. 2004/0161444), and International Pat. Applications Nos. PCT/US2003/040975 and PCT/US2006/006243; all of which are incorporated in their entirety by reference. The composition and polymer scaffold can also be further modified by the addition or incorporation of peptides to the composition or polymer scaffold that promote mineralization or have osteogenic activity or the like. Such peptides are taught in U.S. Pat. Nos. 5,461,034 and 6,479,460, and U.S. patent application Ser. Nos. 60/631,660 and 11/720,427, and International Pat. Applications No. PCT/US2005/043214; all of which are incorporated in their entirety by reference.

Inorganic Component

The inorganic component can be comprise of inorganic materials including but not limited to glass, ceramic, mineral, metallic or semiconductor particles. The inorganic content of the composite is defined as the weight percentage of the inorganic component over the sum of the inorganic and organic components in any given flexible composite, and it is calculated using the following equation:

Inorganic content=Weight(inorganic component)/
 [Weight(inorganic component)+Weight(hydrogel
 repeating units)+Weight(hydrogel crosslinker)]×
 100%

The weight is calculated using the appropriate densities of the monomers and crosslinkers in the organic phase. For example, the weight of HEMA and EGDMA were calculated using the following density values: HEMA (d 1.073 g/mL) and EGDMA (d 1.051 g/mL).

The inorganic component may be comprised of materials that have minimal solubility in the solvent used during polymerization. By "minimal solubility" it is meant that at least more than 90% of the inorganic component remains in a solid state upon interaction with the solvent. One skilled in the art would use a reference such as the *CRC Handbook* to look up the solubilities of the inorganic component in the solvent chosen. For example, if the inorganic component comprises hydroxyapatite (HA; $Ca_{10}(PO_4)_6(OH)_2$) and the solvent is water, the solubility of HA in water at neutral condition is approximately log $[Ca^{2+}]$~−4 (in total molar concentration). While HA has high solubility in water at acidic conditions, it has very low solubility at neutral and basic condition. $10^{-4}$ is not considered to be very soluble, which is why HA may be used in the presence of water at neutral pH.

HA powders may be used for the inorganic component including, but not limited to, commercial polycrystalline HA powders, calcined polycrystalline HA powders, single crystal HA whiskers, HA nanocrystals, and other calcium phosphates (compounds containing Ca, P and O, and possibly C, N, H and additives of F, Cl and Br) including, but not limited to, dicalcium phosphate, tricalcium phosphate, octacalcium phosphate, brushite, dahilite, and hydroxyfluoroapatite. The inorganic component may also comprise Ca, P and O and can further be hydroxylated, carbonated and contain other additives of F, Cl and/or Br. In one embodiment, the inorganic component ratio of Ca to P may be between 0.5 and 4, but more preferably between 1 and 2. In another embodiment, the inorganic component is selected from the group consisting of crystalline, nanocrystalline or amorphous HA, and calcium phosphates that can be further substituted with H, C, N, F, Cl and Br.

The inorganic component may comprise of other materials, including but not limited to ceramics, including oxides and non-oxide ceramics (e.g. $Al_2O_3$, $ZrO_2$, $Si_3N_4$, SiC, ferrites, piezoelectric ceramics such as barium titanate, bioceramics including HA, ceramic superconductors such as YBaCuO), metals and alloys (e.g. Mo, Cu, Ni, stainless steel, Ti6Al4V, Fe—Ni, Co—Cr), glasses including bioactive glasses (e.g. glasses in the Si—Na—Ca—P—O or Si—Na—K—Ca—Mg—P—O systems), and semiconductors including group III, IV, V, VI and VII elements and compounds (e.g. CdS, GaAs, GaP).

In other embodiments, more than one inorganic material may be added to the inorganic composition allowing incorporation at a certain percent into the formed composite for both biomedical and non-biomedical applications. The composite may have different types and/or amounts of dispersed inorganic particles with particle sizes ranging between 1 nm to 10 mm. In some embodiments, wherein the inorganic particle is a fiber or rod-shaped, the inorganic particles may be up to 10 cm in length depending upon the intended use and size of the formed composite.

The inorganic component may be in the form of particles with various shapes and sizes, including but not limited to nanometer and micrometer-scale crystals, whiskers, rods, spheres, tetrapods and polybranched structures and fibers up to centimeter-scale.

Synthesis

The linear chain can be synthesized with two or more repeating subunits of different structures, wherein at least one of the repeating subunit, or first repeating subunit, has a structure that comprises a hydrolytically unstable linkage, such as, if the repeating subunit is polymerized from MA. The other repeating subunit, or second repeating subunit, has a structure that does or does not comprise a hydrolytically unstable linkage. When one of the repeating subunit comprises a hydrolytically unstable linkage and the other repeating subunit does not comprise a hydrolytically unstable linkage, then one of ordinary skill in the art is able to varying the ratio of each repeating subunit to obtain a composition that has a desired rate of biodegradation in a subject or in vitro. One desired rate of biodegradation is the rate in which mammalian cells, or cells of the subject, is able to grow into and occupy the space(s) cleared by the biodegradation. The rate of biodegradation in vitro can be measured using the protocol of Example 2 described below.

A suitable solvent used in the polymerization reaction that does not damage the integrity of either the polymer or the inorganic component, yet provide flexibility to the composite. For example, ethylene glycol or glycerol or other similar high boiling point, non-corrosive, high viscosity non-toxic solvent and/or water may be used as a solvent for polymerization. The higher the amount of ethylene glycol (or glycerol) and the lower the amount of water in the polymerization mixture, the more flexible the prepared composite tends to be.

After the composition is formed, solvent exchange can be performed, either with a large volume of water to get rid of the viscous solvent within the composition, or with large volumes of viscous solvent to get rid of remaining water within the composition. The solvent used during polymerization need not always be a high viscosity, non-toxic solvent, although the presence of it increases the elasticity of the prepared composition. The composition can also be made without the solvent, then perform the solvent exchange with ethylene glycol, glycerol, or water after polymerization to provide composites with flexibility. It has been determined that the complete exchange of solvent, such as ethylene glycol, with water prior to freeze-drying was difficult of achieve in composition possessing very high HA content (greater than 50%). However, prolonged solvent exchange (greater than one day) and repeated hydration/freeze-drying allowed for a complete exchange.

The composition may have an organic-to-inorganic ratio of about 1.0 w/w % to about 99 w/w %, and more preferably from about 10 w/w % to about 90 w/w %. An organic phase comprising a hydrogel monomer, crosslinker, radical initiator, highly viscous solvent and/or water when desired may be mixed together with an inorganic material. The mixture is mixed to form a polymerization mixture having even and good consistency. The polymerization mixture may then be polymerized into a mold for a desired shape and size. The length of time of mixing may vary. However, in most embodiments, the polymerization mixture should be a sufficiently consistent material, which may be checked visually or after polymerization with a method such as scanning electron microscopy (SEM) analysis.

Polymerization may be carried out through various methods of free radical initiation mechanisms, including but not limited to, thermal initiation, photoinitiation, or redox initiation. For polymerization triggered by UV initiation, a photolithographic-like technique using a mask can facilitate the polymerization of composite into various three-dimensionally-shaped composites. For polymerization by thermal or redox initiation, the polymerization mixture may be individually deposited in a mold used to form the desired shape and size of each composition.

In one embodiment, about 0.1-10 wt % (with respect to the monomers) of free radical or hydrogen abstracting photoinitiator may be used to create the bone composition. For example, 1 to 6 wt % (with respect to monomers) of a radical initiator can be used to initiate the polymerization process.

Polymerization of the composition may be achieved using hydrogen abstracting photoinitiators including, but not limited to, benzophenone, 2,2-dimethoxy-2-phenylacetophenone (DMPAP), dimethoxyacetophenone, xanthone, and/or thioxanthone. If solubility of the chosen photoinitiator is poor, desired concentration of the initiator can be achieved by adding a surfactant that enables the homogenization of the initiator in emulsions with higher initiator concentration.

Polymerization may also be carried out by thermal initiation, wherein the thermal initiator is generally a peroxide, a hydroperoxide, peroxo- or an azocompound selected from the group consisting of ammonium persulfate and sodium metasulfite, benzoylperoxide, potassium peroxodisulfate, ammonium peroxodisulfate, t-butyl hydroperoxide, 2,2'-azobisiobutyronitrile (AIBN), and azobisiocyanobutyric acid. The thermally induced polymerization may be performed by heating the polymerization mixture to temperatures between 30° C. and 120° C. Caution should be taken in thermal initiation of polymerization if heat can damage either the formed polymer or the inorganic components.

Polymerization may also be initiated by a redox initiator selected from the group consisting of mixtures of benzoyl peroxide-dimethylaniline, and ammonium peroxodisulfate-N,N,N', N'-tetramethylene-1,2-ethylenediamine. The radical initiators, ammonium persulfate and sodium metasulfite, may be freshly made into aqueous solutions prior to use. These precautions ensure a fast gelation. It is possible, however, to slow down the solidification when necessary by decreasing the amount and concentrations of radical inhibitors used, or with deliberation inclusion of a low concentration of radical inhibitors that typically exist in commercial monomers.

An extended mineral layer may also be grown in the hydrogel polymers. For exemplary purposes only, and not intended to be limiting, the composition and methods described in U.S. patent application Ser. No. 10/740,739 may be used to grow the mineral layer.

Method for polymerization reactions are taught by Sawhney et al. (*Macromolecules* 1993, 26 (4), 581-587), which is incorporated in its entirety by reference, which can be readily adapted to the synthesis of the present invention. Further methods and suitable reagents and polymerization reaction conditions are taught in U.S. patent application Ser. Nos. 60/434,596; 60/655,986; 60/631,660; and 10/740,739 (U.S. Pat. Application Pub. No. 2004/0161444), and International Pat. Applications Nos. PCT/US2003/040975 and PCT/US2006/006243; all of which are incorporated in their entirety by reference.

Applications

The composition synthesized by this method have a nanocrystalline or amorphous mineralization layer with a structure and thickness ideal for bone and/or dental implant applications. Analysis of calcium phosphate coatings on titanium implants has shown that resorption of the coating occurs mostly in the less organized apatite region and stops where the coating has higher crystallinity (Ratner, B. D. *J. Mol. Recognit.* 1996, 9, 617-625). Thus, the amorphous or nanocrystalline layer achieved by this method should promote resorption, bone integration, cell attachment and proliferation. A thin layer of HA with thickness on the order of 1-7 μm provides a sufficient resorption timeframe to allow progressive bone contact with the implant substrate, and is therefore ideal for inducing integration of the material into natural bone (Ratner, B. D. *J. Mol. Recognit.* 1996, 9, 617-625). The favorable properties of the composition obtained using the approach described herein maximize the chance for initiating in vivo remodeling cascades and subsequent positive tissue-implant integration.

In practice it is contemplated that an implantable structure be formed in vitro according to the composition adapted to fit a particular area of bony structure to be repaired or reconstructed. The composition is attached to bone in a vertebrate subject, or deposited on a hydrogel attached to an implant, or deposited on a hydrogel attached to another type of physiological implant. After mineralization according to the present procedures, the mineralized structure is implanted into the subject in the recipient site. Then, the implant is attached to the bony structure under physiological conditions, such as the modification or mediation of osteoclasts and osteoblasts. In a particular embodiment, bone cells, such as osteoclasts and osteoblasts from the subject, are cultured with the implant prior to implantation in the subject. Such applications and extensions of the method would be known or understood by those skilled in the relevant art.

Further applications and uses of the present invention are taught in U.S. patent application Ser. Nos. 60/434,596; 60/655,986; 60/631,660; and 10/740,739 (U.S. Pat. Application Pub. No. 2004/0161444), and International Pat. Applications Nos. PCT/US2003/040975 and PCT/US2006/006243; all of which are incorporated in their entirety by reference.

The invention having been described, the following examples are offered to illustrate the subject invention by way of illustration, not by way of limitation.

EXAMPLE 1

Synthesis of a pHEMA/HA Hydrogel Composite

Figure 1:
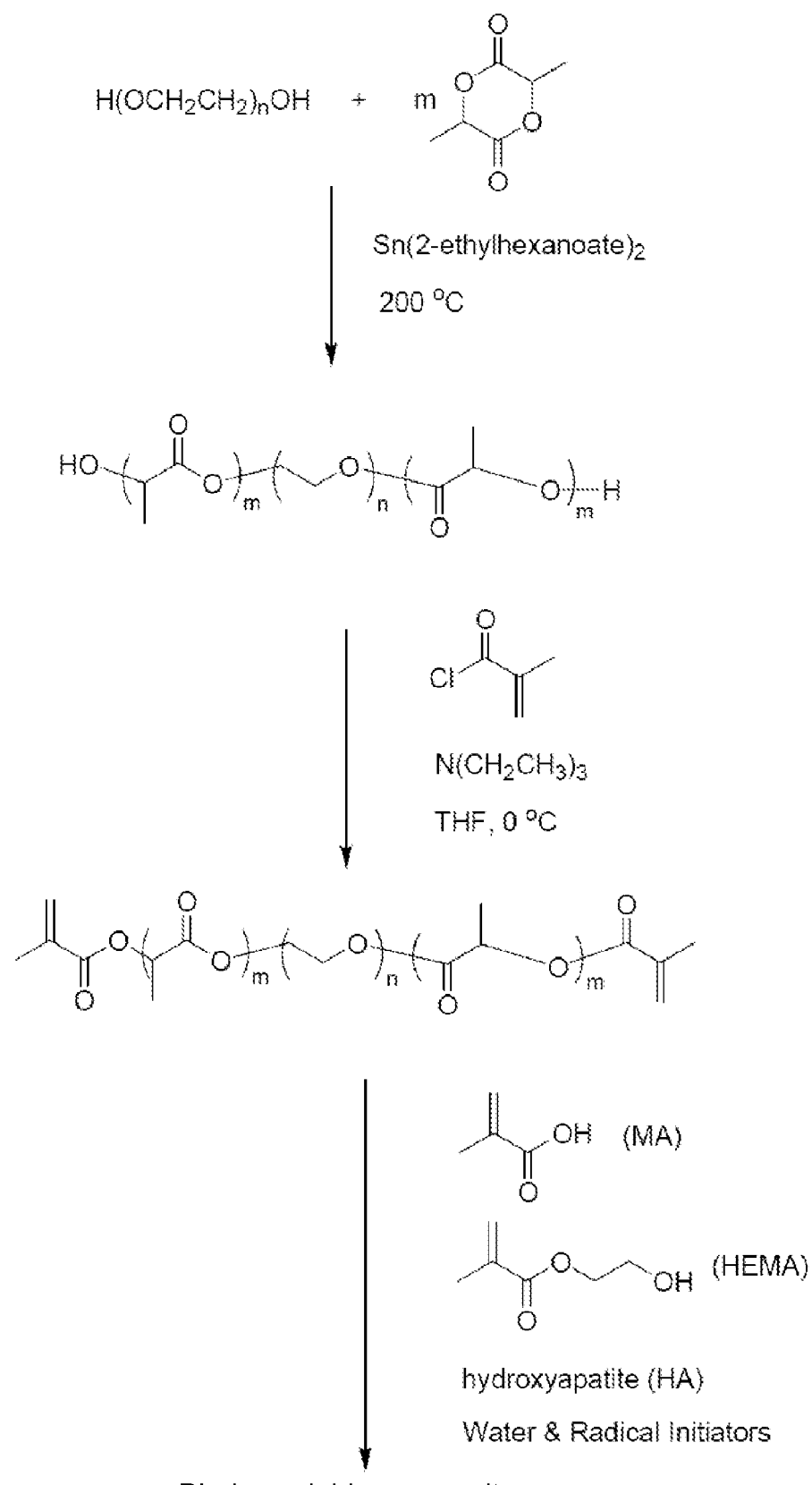
FIG. 1 shows the synthesis of biodegradable crosslinker and formulation of hydrogel/hydroxyapatite (HA) composites. "THF" is tetrahydrofuran.

Lactide monomers are polymerized at both ends of PEG to form polylactic acid (PLA) blocks. The methacrylate polymerization units are capped on both ends of the PLA blocks. The HA mineral is added to the HEMA, MA and the crosslinker mixture, and then is subsequently cured to afford the hydrogel/HA composites, which are biocompatible, degradable and promote bone tissue growth. The synthesis is described in FIG. 1. Other inorganic components such as diverse calcium phosphates or bioactive glasses can be easily added to further manipulate the properties and biodegradation rates of the material. The systemic adjustment of the three reagents would give rise to materials with different decomposition rate and mechanical properties for different applications. (Qiao et al., *Intl. J. Pharm.*, 2005, 294(1-20, 103-112; which is incorporated in its entirety by reference).

EXAMPLE 2

Biodegradation of a pHEMA/HA Hydrogel Composite

Figure 3:
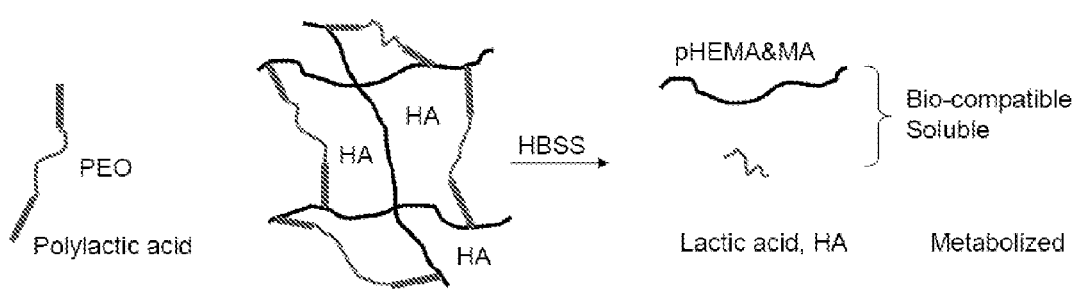
FIG. 3 shows the mechanism of composite degradation. "PEO" is polyethylene oxide.

The composite, the synthesis of which is described in Example 1, is biodegradable as shown by degradation in Hank's Buffered Salt Solution (HBSS). PLA is biodegradable. The decomposition path of the hydrogel/HA composite is shown in FIG. 3. All the components of the composite are water soluble. The PLA portion itself is not water soluble, however the PEG portion attached to the PLA portion renders the entire crosslinker soluble. The lactide connection is gradually hydrolyzed in body fluid to render the hydrogel structure soluble. The final products are bio-compatible and soluble pHEMA, pMA and PEG along with the lactic acid and HA. PLA degrades through hydrolysis and metabolization. As the body fluids encounter the implant, water begins to break down the polymer chains. To complete the degradation, the lactic acid molecules are metabolized into $CO_2$ and $H_2O$. If PG is used, in the body, PG is hydrolyzed into glycolic acid.

Figure 4:
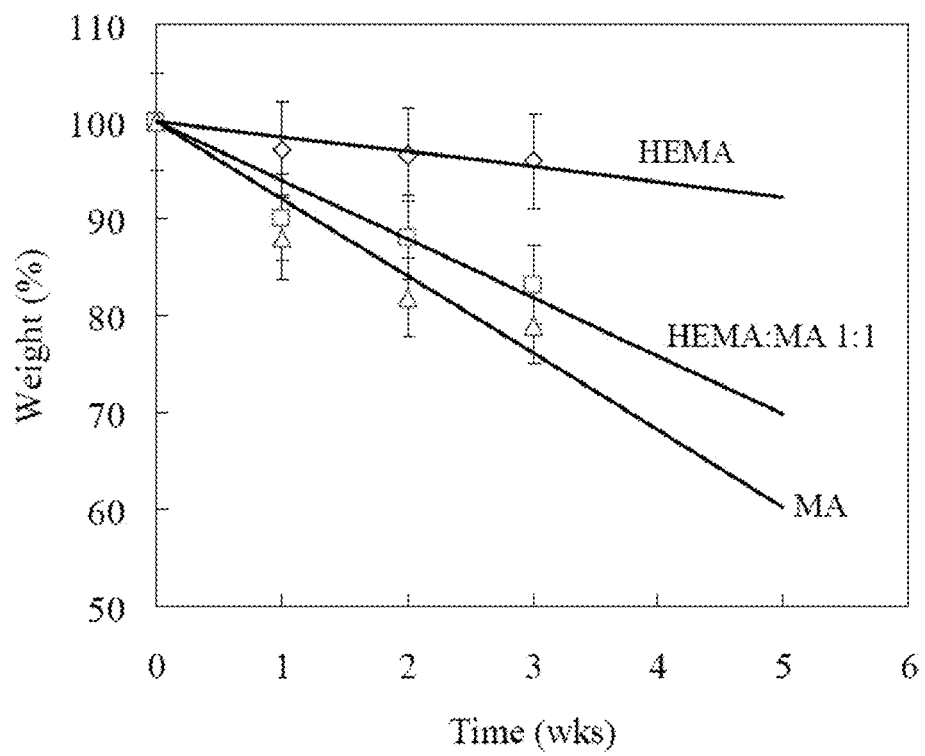
FIG. 4 shows the degradation of hydrogel/HA composite in HBSS at 37° C. The diamond data points represent the percent weight loss of a composite polymerized using HEMA monomers only. The square data points represent the percent weight loss of a composite polymerized using HEMA monomers and MA monomers mixed at a 1:1 ratio. The triangle data points represent the percent weight loss of a composite polymerized using MA monomers only.
Figure 5:
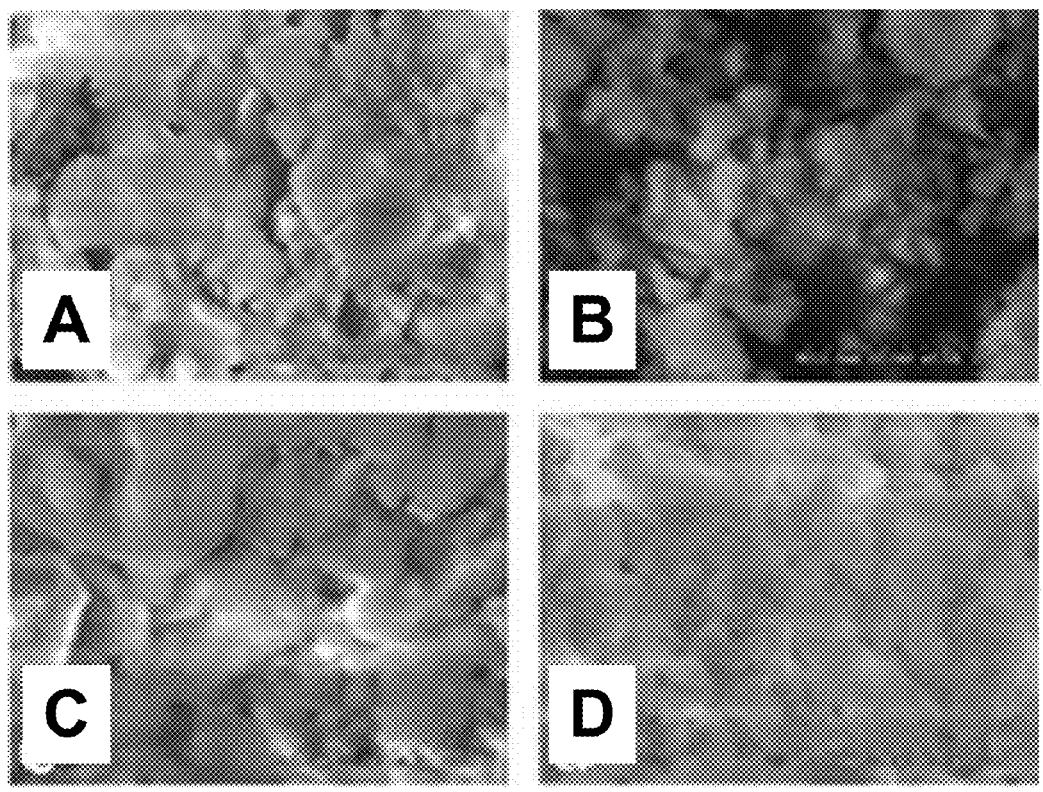
FIG. 5 shows the SEM images of hydrogel/HA composite before (Panels B and D) and after (Panels A and C) immersing in HBSS at 37° C. for 3 weeks. Panels A and B are cross-section images. Panels C and D are surface images.

Hydrogel/HA composites synthesized with varying ratios of HEMA and MA are placed in HBSS at 37° C. for 3 weeks and the percent weight of the composites are measured weekly. The result of such an experiment is shown in FIG. 4. The pHEMA hydrogel/HA composites degrade slower, whereas the pMA hydrogel degrade much faster, due to different water affiliation properties of MA and HEMA. As such, hydrogels of different compositions of pHEMA, pMA and crosslinker can be formulated to control the rate of degradation. The degradation process in HBSS starts from hydrolysis of the PLA crosslinker, followed by dissolution of the pHEMA and pMA into the HBSS. SEM images of hydrogel/HA composites before and after immersing in HBSS at 37° C. for 3 weeks indicate that the sample immersed in HBSS has less polymer and more exposed HA compared to the non-degraded sample (see FIG. 5). The interior of the hydrogel decomposes and dissolves much slower than the surface, which is exposed to the HBSS. HBSS is commercially available from Invitrogen Corp. (Carlsbad, Calif.).

Figure 7:
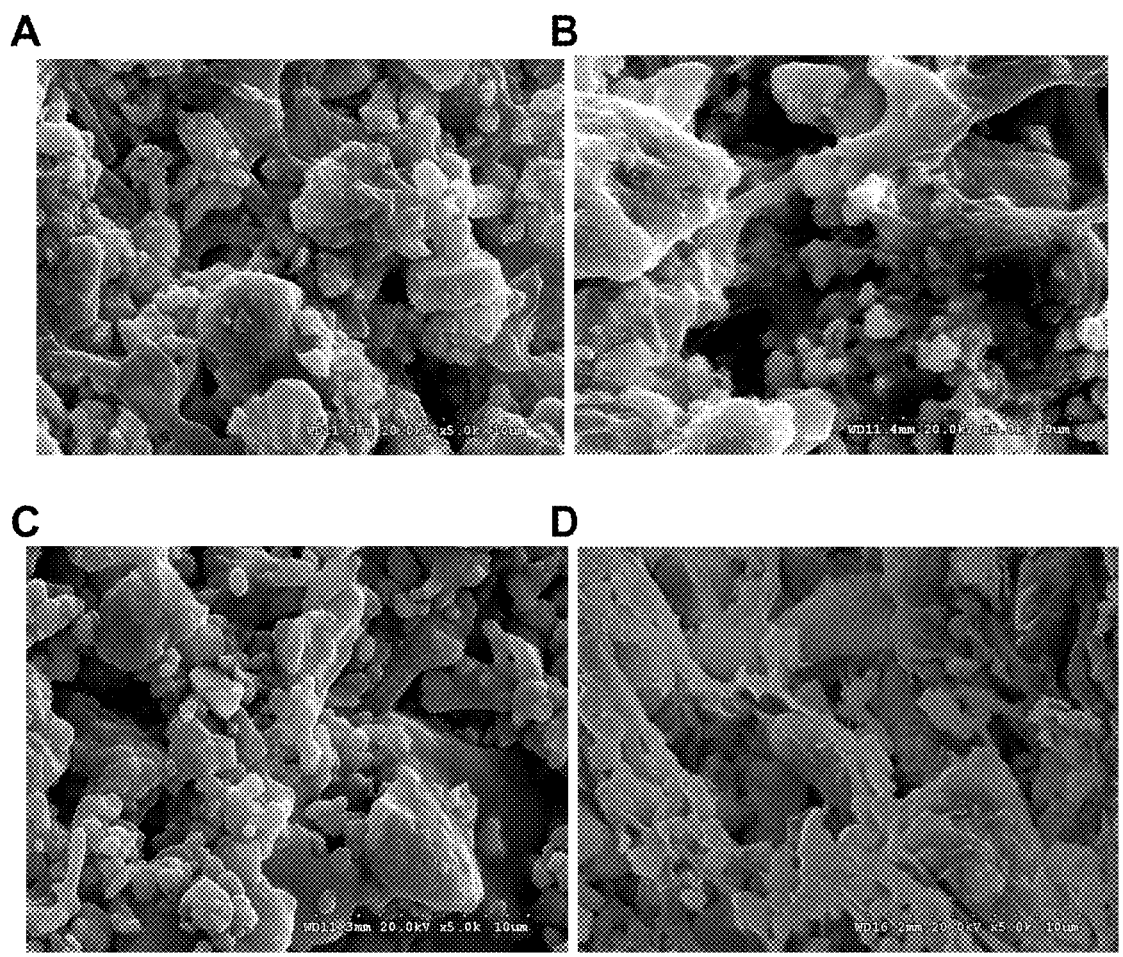
FIG. 7 shows SEM images of hydrogel/HA composites before (Panels A and B) and after (Panels C and D) in vitro test in HBSS at 37° C. for 8 weeks. Panels A and C are surface images. Panels B and D are cross-section images.

FIG. 7 shows SEM images of hydrogel/HA composites before (Panels A and B) and after (Panels C and D) in vitro test in HBSS at 37° C. for 8 weeks. Panels A and C are surface images. Panels B and D are cross-section images. These results indicate that the sample immersed in HBSS has less polymer and more exposed HA compared to the non-degraded sample

EXAMPLE 3

Growth of Cells into a pHEMA/HA Hydrogel Composite

The growth of cells into biodegraded pHEMA/HA hydrogel composite can be performed using the following method as adapted from S. Foppiano et al. (Bioactive glass coatings affect the behavior of osteoblast-like cells, *Acta Biomater.* (2007), doi:10.1016/j.actbio.2007.02.011; in press, e-publication on Apr. 25, 2007), which is incorporated in its entirety by reference.

The pHEMA/HA hydrogel composite, along with suitable controls, is preconditioned in 4 ml of filter sterilized simulated body fluid (SBF). The ion concentration of SBF is 142 M $Na^+$, 5 mM of $K^+$, 2.05 mM of $Ca^{2+}$, 1.5 mM of $Mg^{2+}$, 148 mM of $Cl^-$, 4.2 mM of $HCO_3^-$, and 1 mM of $HPO_4^{2-}$. The samples are preconditioned for 2 weeks at 37° C., changing the solution after 1 week. Samples are rinsed with phosphate-buffered saline (PBS) prior to cell seeding.

MC3T3.E1.4 mouse osteoblast-like cells are grown in an incubator at 37° C. and 5% CO2 atmosphere, in α-modified Eagle's medium (α-MEM) supplemented with 10% fetal calf serum (FCS) and 1% antibiotics (penicillin and streptomycin) (full medium) and passaged every 4-5 days. Cells are plated at an initial density of 50,000 cells $cm^{-2}$ (Gomez-Vega et al. 1. *Processing. Biomaterials* 2000, 21(2), 1054-11; which is incorporated in its entirety by reference).

Cells are seeded in 30 μl aliquots on the center of sample and control materials. After 10 minutes the wells are gently flooded with the medium (1 ml per well). Three hours after flooding, the supernatant containing the non-adhering cells is removed, and is replaced with fresh medium. The number of adhering cells is assayed using a commercial kit (CellTiter 96® Promega Corp., Madison, Wis.), based on the metabolic activity of living cells (3-(4,5-dimethylthiazol-2-yl)-2,5-diphenyl tetrazolium bromide) (MTT assay). The MTT solution added to each well is incubated for 4 hours at 37° C. Typical results of this assay should indicate significant adherence of the MC3T3.E1.4 mouse osteoblast-like cells on the pHEMA/HA hydrogel composite.

Sample of the pHEMA/HA hydrogel composite incubated with the cells are taken once a week to observe the rate of biodegradation and the rate of growth and proliferation of cells within the composite. Samples can be taken up to 8 weeks or 12 weeks. Each sample of the pHEMA/HA hydrogel composite is sectioned and SEM images taken of the interior of the composite. Typical results should indicate degradation of the interior of the pHEMA/HA hydrogel composite and the significant growth and proliferation of the MC3T3.E1.4 mouse osteoblast-like cells into the composite. Typical results should also indicate that the HA stays while the polymer scaffold is degraded.

EXAMPLE 4

MA/HEMA Ratio Controls the Decomposition Rate of the Hydrogel/HA Composites

Figure 6:
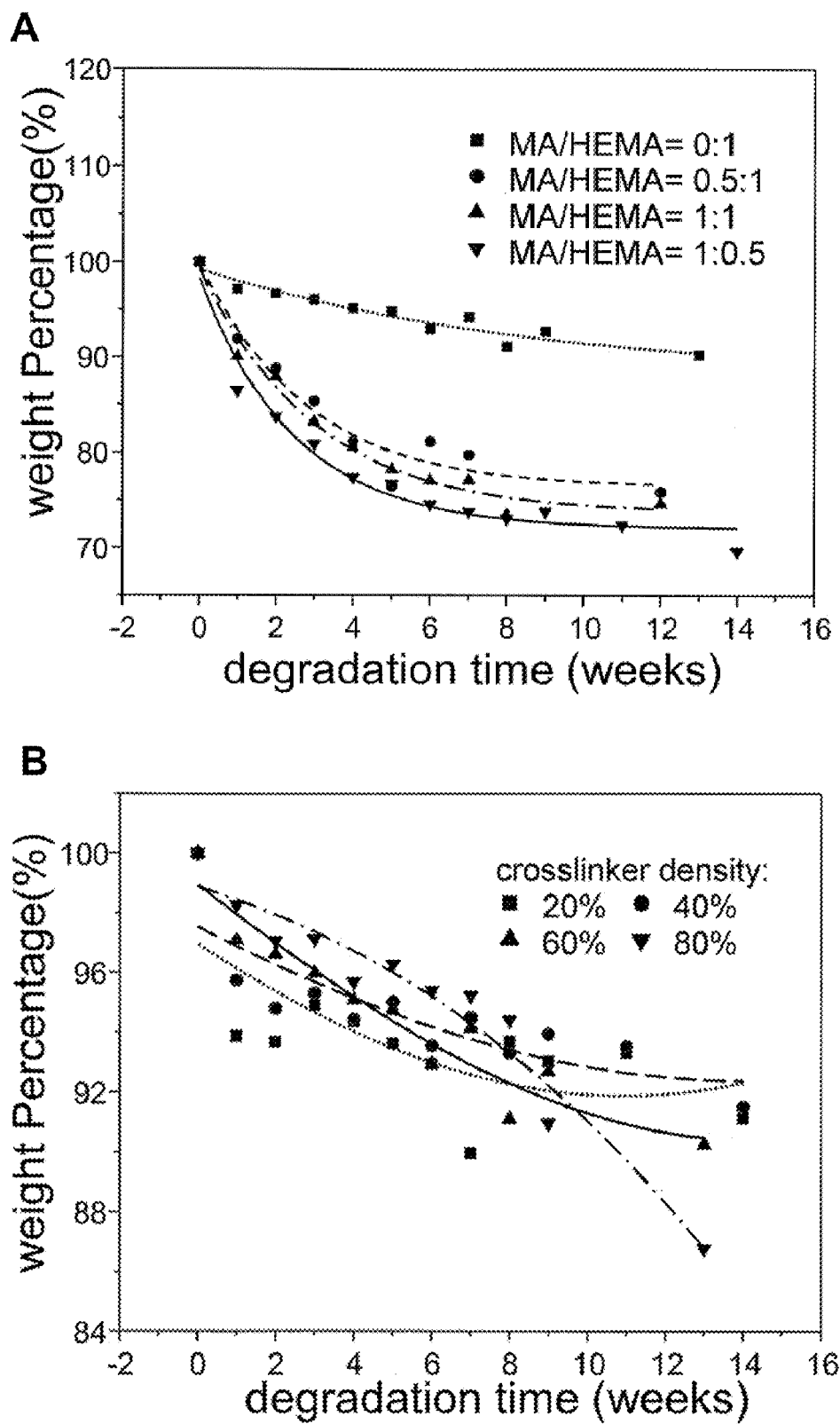
FIG. 6 shows the weight percentage over degradation time. Panel A shows the MA/HEMA ratio controls the decomposition rate of the hydrogel/HA composites. The values for the MA/HEMA ratio equal to 0:1 are indicated by "■" (dotted line). The values for the MA/HEMA ratio equal to 0.5:1 are indicated by "●" (dashed line). The values for the MA/HEMA ratio equal to 1:1 are indicated by "▲" (-•-•- line). The values for the MA/HEMA ratio equal to 1:0.5 are indicated by "▼" (solid line). Panel B shows the cross-linker density controls the decomposition rate of the gel/HA composites. The values for the cross-linker density equal to 20% are indicated by "■" (dotted line). The values for the cross-linker density equal to 40% are indicated by "●" (dashed line). The values for the cross-linker density equal to 60% are indicated by "▲" (solid line). The values for the cross-linker density equal to 80% are indicated by "▼" (-•-•- line).

A series of hydrogel/HA composites are prepared using lactide-based PEG copolymer as a precursor. These hydrogel/HA composites are biodegradable. The decomposition rate can be controlled by the proportion of HEMA and MA within the hydrogel material. The early stage degradation rate increase with increasing MA content in the composite hydrogel, i.e., the MA/HEMA ratio (see FIG. 6, Panel A).

EXAMPLE 5

Cross-Linker Density Controls the Decomposition Rate of the Hydrogel/HA Composites A series of hydrogel/HA composites are prepared using lactide-based PEG copolymer as a precursor. These hydrogel/HA composites are biodegradable. The late stage degradation rate increase with increasing cross-linker content in the composite hydrogel, i.e., the cross-linker density (see FIG. 6, Panel B).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A biodegradable synthetic bone composition comprising:
    (a) a biodegradable hydrogel polymer scaffold comprising a plurality of linear chains, wherein each linear chain comprises a crosslinker which links the linear chain to another linear chain, and each crosslinker comprises a hydrolytically unstable linkage; wherein each linear chain of the biodegradable hydrogel polymer scaffold comprises one or more repeating subunits of different structures with the following structure:

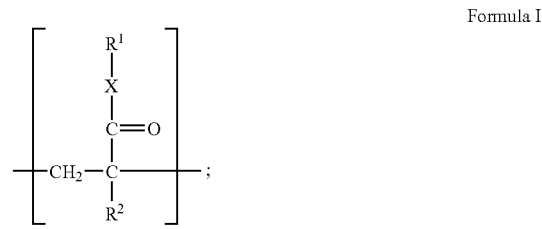

Formula I wherein $R^1$ is H, a lower alkyl, wherein a partial number of the $R^1$ of the biodegradable hydrogel polymer scaffold are negative charges; R² is H or a lower alkyl, and X is O, S or NH; and each crosslinker comprises the following structure:

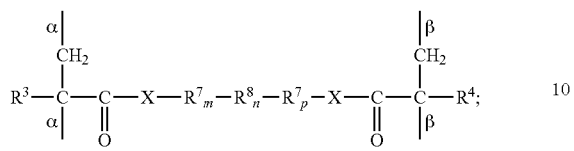

Formula III wherein R³ is H or a lower alkyl; R⁴ is H or a lower alkyl; X is O, S or NH; R⁷ is —R⁹COO—, —R⁹C(OR¹⁰)(OR¹¹)O—, —R⁹CONH—, or —R⁹CON(R¹⁰)—; R⁸ is —$C_qH_{2q}$—O— wherein q is a integer from 0 to 3; m, n, and p are each independently an integer from 1 to 10,000; R⁹ is —$C_rH_{2r}$—, wherein r is an integer from 0 to 3; R¹⁰ and R¹¹ are each independently —$C_sH_{2s}$—CH₃, wherein s is an integer from 0 to 3; and the α bonds connect two repeating subunits of a first linear chain, and the β bonds connect two repeating subunits of a second linear chain, wherein the amount of the crosslinker is from 20% to 80% of the polymer scaffold; and (b) an inorganic component.

2. The composition of claim 1, wherein X is O.

3. The composition of claim 1, wherein R¹ is H, —CH₂OH, —CH₂CH₂OH, —CH₂CH₂CH₂OH, —CH(CH₃)CH₂OH, —CH₂CH(CH₃)OH, —C(CH₃)₂OH, or —C₄H₈—OH.

4. The composition of claim 1, wherein R² is H.

5. The composition of claim 1, wherein for a first repeating subunit X is O, R² is H, and R¹ is H; and for a second repeating subunit X is O, R² is H, and R¹ is —CH₂CH₂OH.

6. The composition of claim 1, wherein R³ is H, —CH₂OH, —CH₂CH₂OH, —CH₂CH₂CH₂OH, —CH(CH₃)CH₂OH, —CH₂CH(CH₃)OH, —C(CH₃)₂OH, or —C₄H₈—OH.

7. The composition of claim 1, wherein R⁴ is H, —CH₂OH, —CH₂CH₂OH, —CH₂CH₂CH₂OH, —CH(CH₃)CH₂OH, —CH₂CH(CH₃)OH, —C(CH₃)₂OH, or —C₄H₈—OH.

8. The composition of claim 1, wherein each R³ and R⁴ is H.

9. The composition of claim 1, wherein each R⁷ is —CH₂COO—, —CH(CH₃)COO—, or —CH(CH₂CH₃)COO—, and each R⁸ is —CH₂CH₂O—, —CH₂CH₂CH₂O—, —CH(CH₃)CH₂O—, —CH₂CH(CH₃)O—, —C(CH₃)₂O—, or —C₄H₈—O—.

10. The composition of claim 1, X is O, each R³ and R⁴ is H, R⁷ is —CH(CH₃)COO—, and R⁸ is —CH₂CH₂O—.

11. The composition of claim 1, wherein said inorganic component comprises polycrystalline hydroxyapatite (HA) powders, calcined polycrystalline HA powders, single crystal HA whiskers, HA nanocrystals, or calcium phosphate.

12. The composition of claim 1, wherein the inorganic component comprises HA ($Ca_{10}(PO_4)_6(OH)_2$).

13. A bone or dental implant comprising the composition of claim 1, wherein the composition is a degraded composition having undergone biodegradation, and mammalian cells have grown into the biodegraded composition.

14. The implant of claim 13, wherein the mammalian cells are human cells.

15. The implant of claim 13, wherein the mammalian cells are mammalian osteoblasts.

16. A method for synthesizing a biodegradable synthetic bone composition comprising:

(a) providing a polymerization mixture comprising a crosslinker which polymerizes into the following structure:

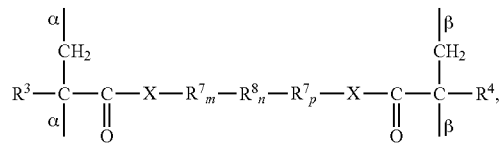

Formula III wherein R³ is H or a lower alkyl; R⁴ is H or a lower alkyl; X is O, S or NH; R⁷ is —R⁹COO—, —R⁹C(OR¹⁰)(OR¹¹)O—, —R⁹CONH—, or —R⁹CON(R¹⁰)—; R⁸ is —$C_qH_{2q}$—O— wherein q is a integer from 0 to 3; m, n, and p are each independently an integer from 1 to 10,000; R⁹ is —$C_rH_{2r}$—, wherein r is an integer from 0 to 3; R¹⁰ and R¹¹ are each independently —$C_sH_{2s}$—CH₃ wherein s is an integer from 0 to 3; and the α bonds connect two repeating subunits of a first linear chain, and the β bonds connect two repeating subunits of a second linear chain, wherein the amount of the crosslinker is from 20% to 80% of the polymer scaffold, one or more repeating subunits of different structures which polymerizes into the following structure:

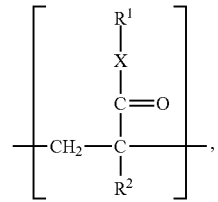

Formula I wherein R¹ is H, a lower alkyl, wherein a partial number of the R¹ of the biodegradable hydrogel polymer scaffold are negative charges; R² is H or a lower alkyl, and X is O, S or NH, an initiator to initiate polymerization of the cross-linker and the one or more repeating subunits, and an inorganic component; and (b) polymerizing the polymerization mixture under a condition suitable for polymerization of the cross-linker and the one or more repeating subunits to form the biodegradable synthetic bone composition.

17. The method of claim 16, further comprising the step of:

(c) adding a mammalian cell to the biodegradable synthetic bone composition; and (d) culturing the mammalian cells in the biodegradable synthetic bone composition for growth of the mammalian cell.

18. The method of claim 17, wherein the mammalian cells are human cells.

19. The method of claim 18, wherein the mammalian cells are mammalian osteoblasts.

20. The method of claim 16, wherein the one or more repeating subunits of different structures of Formula I comprises 2-hydroxyethyl methylacrylate (HEMA) and methylacrylate (MA).

21. The method of claim 16, wherein said inorganic component comprises polycrystalline hydroxyapatite (HA) powders, calcined polycrystalline HA powders, single crystal HA whiskers, HA nanocrystals, or calcium phosphate.

22. The method of claim 16, wherein the inorganic component comprises HA ($Ca_{10}(PO_4)_6(OH)_2$).

* * * * *